United States Patent [19]

Boar et al.

[11] Patent Number: 5,607,956
[45] Date of Patent: Mar. 4, 1997

[54] 1-HETEROAZOLYL-1-HETEROCYCLYL ALKANE DERIVATIVES AND THEIR USE AND THEIR USE AS NEUROPROTECTIVE AGENTS

[75] Inventors: Robin B. Boar, Herts; Alan J. Cross, Surrey; Duncan A. Gray, Powys; Richard A. Green, Oxon, all of Great Britain

[73] Assignee: Astra Aktiebolag, Sodertalje, Sweden

[21] Appl. No.: 459,847

[22] Filed: Jun. 2, 1995

Related U.S. Application Data

[62] Division of Ser. No. 379,506, Jan. 30, 1995.

[30] Foreign Application Priority Data

Jul. 6, 1993 [SE] Sweden .................... 9302332

[51] Int. Cl.$^6$ .................... A61K 31/41; A61K 31/42; A61K 31/425
[52] U.S. Cl. .................... 514/365; 514/361; 514/362; 514/363; 514/364; 514/372; 514/374; 514/378; 514/381; 514/383; 514/385; 514/396; 514/399; 514/400; 514/403; 514/406; 514/408; 514/423; 514/427; 514/428
[58] Field of Search .................... 514/361, 362, 514/363, 364, 365, 372, 374, 378, 381, 383, 385, 396, 399, 400, 403, 406, 408, 423, 427, 428

[56] References Cited

U.S. PATENT DOCUMENTS 5,068,237 11/1991 Hobbs .................... 514/365

FOREIGN PATENT DOCUMENTS 0091726 10/1983 European Pat. Off. .
9313083 7/1983 WIPO .

OTHER PUBLICATIONS

Dondoni et al., "Synthesis of (Trimethylsilyl) thiazoles and Reactions with Carbonyl Compounds. Selectivity Aspects and Synthetic Utility," J. Org. Chem. vol. 53 (1988).
Patent Abstacts of Japan, vol. 13, No. 592, C–671, abstract of JP, A, 1–249760 (Yamaha Corp.), Oct. 5, 1989.
CA 101:191771p (1,3–Dialkyl–5–amino–1H–pyrazol–4–yl)arylmethanones. A series . . . depressants. Butler et al., p. 756, 1984.
CA 116:106294c Preparation . . . psychoanaleptics Hobbs, p. 779, 1992.
CA 119:271158f (Amidazolylalkyl) . . . agonists. Shih et al., p. 998, 1993.

Primary Examiner—Joseph McKane
Attorney, Agent, or Firm—White & Case

[57] ABSTRACT

The present invention relates to novel heterocyclic compounds having the general formula (1)

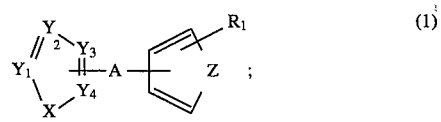

(1)

geometric and optical isomers and racemates thereof where such isomers exist, as well as pharmaceutically acceptable acid addition salts thereof and solvates thereof;
having therapeutic activity, processes and intermediates for their preparation, pharmaceutical formulations containing said compounds and the medicinal use of said compounds.

1 Claim, No Drawings

1-HETEROAZOLYL-1-HETEROCYCLYL ALKANE DERIVATIVES AND THEIR USE AND THEIR USE AS NEUROPROTECTIVE AGENTS

This application is a divisional of application Ser. No. 08/379,506, still pending filed on Jan. 10, 1995.

FIELD OF THE INVENTION

The present invention relates to novel heterocyclic compounds having therapeutic activity, processes and intermediates for their preparation, pharmaceutical formulations containing said compounds and the medicinal use of said compounds.

BACKGROUND OF THE INVENTION

There exists a large group of acute and chronic neuropsychiatric disorders for which safe and clinically effective treatments are not currently available. This diverse group of disorders encompasses a broad spectrum of initial events which are characterised by the initiation of progressive processes that sooner or later lead to neuronal cell death and dysfunction. Stroke, cerebral ischaemia, trauma or a neurodegenerative disease such as Alzheimer's disease or Parkinson's disease are all commonly occurring conditions that are associated with neurodegeneration of the brain and/or spinal cord.

The ongoing search for potential treatments of neurodegenerative disorders has involved investigation of excitatory amino acid antagonists, inhibitors of lipid peroxidation, calcium channel antagonists, inhibitors of specific pathways of the arachidonic acid cascade, kappa opioid agonists, adenosine agonists, PAF antagonists and diverse other agents. At the present time there is no consensus of the relative importance of the role played by compounds belonging to any of these general classes.

In a series of papers concerned with the chemistry of pyrrole dyes, A. Treibs and co-workers (Leibig's Ann. Chem., 1957, 602, 153–183 and 1958, 612, 242–264) have characterised a number of 1,1-dipyrrole alkenes of the following formula:

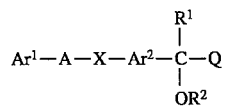

n = 1 or 2
R = various groups

In a paper on the reactions of fulvenes with 1,3-dipolar compounds (Leibig's Ann. Chem., 1981, 491–501), the following compound is disclosed:

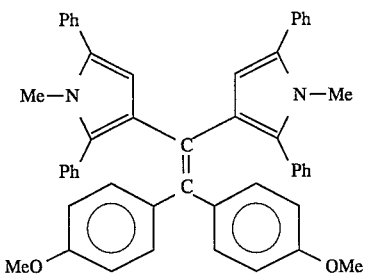

No pharmacological activity is associated with any of the above compounds. The substitution pattern of the above compounds places them outside the scope of the present invention.

European patent application EP 293220 and J. Heterocyclic Chem., 1990, 27, 1933–40 disclose 1,5-diaryl pyrazoles of formula:

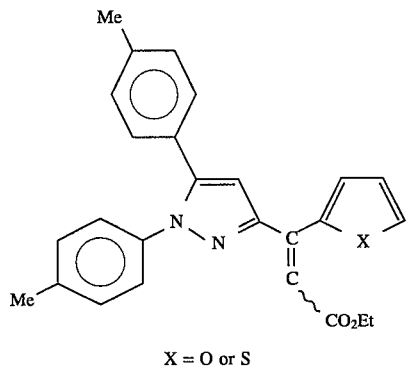

X = O or S

Said compounds are related to possible anti-inflammatory agents. Such activity requires the presence of the 1,5-diaryl substituents, a feature which excludes these compounds from the scope of the present invention.

In patent application EP 351 194 compounds of the general formula:

$$Ar^1-A-X-Ar^2-\underset{OR^2}{\overset{R^1}{\underset{|}{\overset{|}{C}}}}-Q$$

wherein Q is thiazolyl, $Ar^1$ is aryl of up to 10 carbon atoms, $Ar^2$ is 6-membered aryl, including pyridyl, X is O, S, SO, $SO_2$ or NH and A is a direct link to X or is (1-6C)alkylene, (3-6C)alkenylene, (3-6C)alkynylene or cyclo(3-6C)alkylene are disclosed as 5-lipoxygenase inhibitors. The substituent $Ar^1$-A-X is not included within the scope of $R^1$ in claim 1 of the present invention.

Monatsh. Chem. 1987, 118, 1031–1038, discloses a compound of formula:

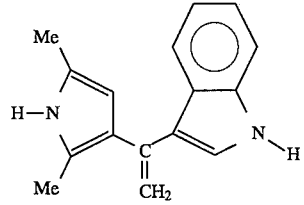

and J. Heterocyclic Chem., 1989, 26, 1869–1873 describes compounds of formulae

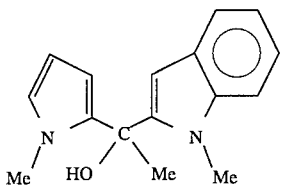

and

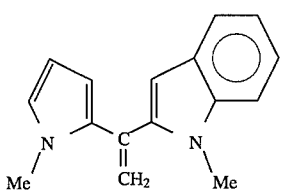

No pharmacological activity is associated with the compounds in either of these two papers. These three specific compounds are deleted from the scope of the present invention by a disclaimer in claim 1.

In Zh. Obshch. Khim., 1962, 32, 2664–2670 (Chem. Abs. 58: 9057h), 1-(4-pyridyl)-1-(2-thiazolyl)ethanol is described. In Zh. Obshch. Khim., 1963, 33, 825–828 (Chem.Abs. 59: 8722a), 1-(2-pyridyl)-1-(2-thiazolyl)ethanol is described. No pharmacological activity is associated with either of these two compounds. These two specific compounds are deleted from the scope of the present invention by a disclaimer in claim 1.

THE PRESENT INVENTION

A primary objective of the present invention is to provide structurally novel heterocyclic compounds which by virtue of their pharmacological profile are expected to be of value in the treatment of acute and chronic neuropsychiatric disorders characterised by progressive processes that sooner or later lead to neuronal cell death and dysfunction. Such disorders include stroke; cerebral ischaemia; dysfunctions resulting from brain and/or spinal trauma; hypoxia and anoxia, such as from drowning, and including perinatal and neonatal hypoxic asphyxial brain damage; multi-infarct dementia; AIDS dementia; neurodegenerative diseases such as Alzheimer's disease, Parkinson's disease, Huntington's chorea, epilepsy, multiple sclerosis and amytrophic lateral sclerosis; brain dysfunction in connection with surgery involving extracorporeal circulation or in connection with brain surgery, including endarterectomy of the carotid arteries; and CNS dysfunctions as a result of exposure to neurotoxins or radiation. This utility is manifested, for example, by the ability of these compounds to inhibit delayed neuronal death in the gerbil bilateral occlusion model of ischaemia.

The present invention relates to a compound having the general formula (1)

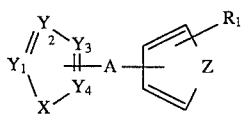 (1)

wherein:
X is O, S, Se or $NR_2$;
$Y_1, Y_2, Y_3, Y_4$ independently are N or $CR_2$;
Z is O, S, Se, $NR_2$ or C=N;

$R_1$ is one or more groups selected from H, lower alkyl, lower acyl, halogen, lower alkoxy or $CF_3$ or $R_1$ and the ring

together represent a fused benzo ring optionally further substituted;

$R_2$ is H, lower alkyl, lower alkoxy-lower alkyl, hydroxy-lower alkyl, lower acyloxy-lower alkyl, aryl-lower alkyl or $CF_3$ and when more than one $R_2$ groups are present these may be selected independently;

and

A is

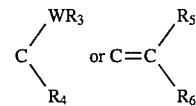

wherein
W is O, S, NH or N-lower alkyl,
$R_3$ is H, lower alkyl or lower acyl,
$R_4$ is lower alkyl, aryl-lower alkyl, cyclopropyl or lower perfluoroalkyl,
or $R_3$ and $R_4$ together form a ring

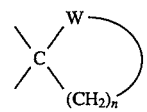

wherein n is 2, 3 or 4,
$R_5$ and $R_6$ independently are H, lower alkyl, or aryl-lower alkyl;
with the proviso that at least one of X, $Y_1$, $Y_2$, $Y_3$ or $Y_4$ is nitrogen and that the ring

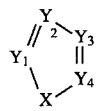

is not 1-methyl-2-imidazolyl;

geometrical and optical isomers and racemates thereof where such isomers exist, as well as pharmaceutically acceptable acid addition salts thereof and solvates thereof;

and with the proviso that the following five compounds are excluded:
  1-(3-indolyl)-1-(2,5-dimethyl-3-pyrrolyl)ethene;
  1-(1-methyl-2-indolyl)-1-(1-methyl-2-pyrrolyl)ethene;
  1-(1-methyl-2-indolyl)-1-(1-methyl-2-pyrrolyl)ethanol;
  1-(4-pyridyl)-1-(2-thiazolyl)ethanol;
  1-(2-pyridyl)-1-(2-thiazolyl)ethanol.

The expression "pharmaceutically acceptable acid addition salts" is intended to include but is not limited to such salts as the hydrochloride, hydrobromide, hydroiodide, nitrate, hydrogen sulphate, dihydrogen phosphate, ethanedisulphonate, mesylate, fumarate, maleate and succinate.

Preferred embodiments of this invention relate to compounds having the general formula (2)

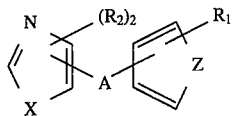

wherein:

X is O or S;

and A, Z, $R_1$ and $R_2$ are as previously defined above.

More preferred embodiments of this invention relate to compounds having the general formula (3)

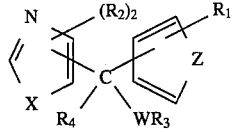

wherein:

X and Z independently are O or S;

W is O;

and $R_1$, $R_2$, $R_3$, $R_4$ are as previously defined above;

and to compounds having the general formula (4)

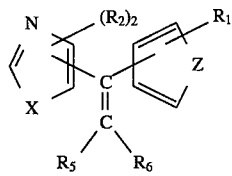

wherein:

X and Z independently are O or S;

and $R_1$, $R_2$, $R_5$ and $R_6$ are as previously defined above.

Analogous compounds wherein X is Se, for example, 1-(3-furyl)-1-(4-methyl-5-selenazolyl)ethanol and 1-(2-selenazolyl)-1-(3-thienyl)ethanol, are specifically included within the scope of the invention.

Throughout the specification and the appended claims, a given chemical formula or name shall encompass all geometrical and optical isomers and racemates thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term "lower alkyl" denotes a straight or branched alkyl group having from 1 to 6 carbon atoms. Examples of said lower alkyl include methyl, ethyl, n-propyl, isopropyl, n-butyl, isobutyl, t-butyl and straight- and branched-chain pentyl and hexyl.

Unless otherwise stated or indicated, the term "lower perfluoroalkyl" denotes a straight or branched alkyl group having from 1 to 4 carbon atoms fully substituted by fluorine. Examples of said lower perfluoroalkyl groups include trifluoromethyl, pentafluoroethyl and heptafluoroisopropyl.

Unless otherwise stated or indicated, the term "lower acyl" denotes a straight or branched acyl group having from 1 to 6 carbon atoms. Examples of said lower acyl include formyl, acetyl, propionyl, iso-butyryl, valeryl, and pivaloyl.

Unless otherwise stated or indicated, the term "lower alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight-and branched-chain pentoxy and hexoxy.

Unless otherwise stated or indicated, the term "hydroxy-lower alkyl" denotes a lower alkyl group as defined above substituted by a hydroxy group. Examples of said hydroxy-lower alkyl include hydroxymethyl, 1-hydroxyethyl and 2-hydroxyethyl.

Unless otherwise stated or indicated, the term "lower acyloxy-lower alkyl" denotes a lower alkyl group as defined above substituted by an oxygen atom which itself bears a lower acyl group as defined above. Examples of said lower acyloxy-lower alkyl include acetoxymethyl, propionyloxymethyl, 1-acetoxyethyl and 2-acetoxyethyl.

Unless otherwise stated or indicated, the term "halogen" shall mean fluorine, chlorine, bromine or iodine.

Unless otherwise stated or indicated, the term "lower alkoxy-lower alkyl" denotes a lower alkyl group as defined above substituted by a lower alkoxy group as defined above. Examples of said lower alkoxy-lower alkyl include methoxymethyl, ethoxymethyl, methoxyethyl and ethoxyethyl.

Unless otherwise stated or indicated, the term "aryl" denotes a phenyl, naphthyl, furyl, thienyl, pyridyl or pyrrolyl group, itself optionally substituted.

Unless otherwise stated or indicated, the term "aryl-lower alkyl" denotes a lower alkyl group as defined above substituted by an aryl group as defined above. Examples of said aryl-lower alkyl include benzyl, phenethyl, phenylpropyl, 4-fluorophenylmethyl, furfuryl, 3-furylemethyl, tolylethyl and thenyl.

Unless otherwise stated or indicated, the term "fused benzo ring" denotes a fully unsaturated five-membered heterocyclic ring containing one heteroatom fused onto a benzene ring. Examples of said fused benzo ring include benzofuranyl, benzo[b] thienyl and indolyl.

Among the most preferred compounds of formula (1) according to the present invention are:

1-(3-furyl)-1-(4-methyl-5-oxazolyl)ethanol;

1-(4-methyl-5-oxazolyl)-1-(3-thienyl)ethanol;

1-(3-furyl)-1-(4-methyl-5-thiazolyl)ethanol;

1-(2,4-dimethyl-5-oxazolyl)-1-(3-furyl)ethanol;

1-(2,4-dimethyl-5-thiazolyl)-1-(3-furyl)ethanol;

1-(4-methyl-5-thiazolyl)-1-(3-thienyl) ethanol;

1-(2-ethyl-4-methyl-5-oxazolyl)-1-(3-thienyl)ethanol;

1-(2,5-dimethyl-4-oxazolyl)-1-(3-furyl)ethanol;

1-(4-methyl-5-thiazolyl)-1-(2-thienyl)ethanol;

1-(5-thiazolyl)-1-(3-thienyl)ethanol;

1-(3-furyl)-1-(4-methyl-5-oxazolyl)ethene;

1-(3-furyl)-1-(4-methyl-5-oxazolyl)-1-propene;

1-(2,4-dimethyl-5-oxazolyl)-1-(3-furyl)ethene;

1-(2-furyl)-1-(4-methyl-5-oxazolyl)ethanol;

1-(2-thiazolyl)-1-(2-thienyl)ethanol;

1-(2-thiazolyl)-1-(3-thienyl)ethanol;

1-(3-furyl)-1-(4-methyl-2-oxazolyl)-2,2,2-trifluroethanol;

1-(4-methyl-2-oxazolyl)-1-(3-thienyl)ethanol;

1-(2,4-dimethyl-5-oxazolyl)-1-(3-furyl)-2,2,2-trifluroethanol;

1-(3-furyl)-1-(4-methyl-5-oxazolyl)ethylamine;

1-(2-thiazolyl)-1-(3-thienyl)ethylamine;

and pharmaceutically acceptable acid addition salts or solvates thereof.

The present invention also relates to processes for preparing the compound having formula (1). Throughout the following general description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups are described, for example, in "Protective Groups in Organic Synthesis", T.W. Greene, Wiley-Interscience, New York, 1981.

Said compound wherein A is

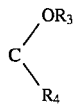

may be prepared by (a) reacting a compound of general formula (5) with an organometallic derivative of general formula (6)

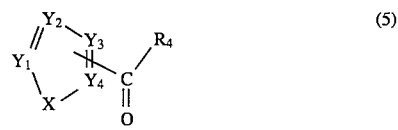

or (b) reacting a compound of general formula (7) with an organometallic derivative of general formula (8)

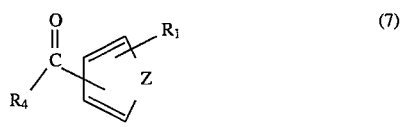

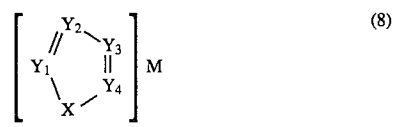

or (c) reacting a compound of general formula (9) with an organometallic derivative of general formula R₄M

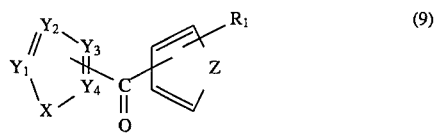

and quenching the reaction mixture with a proton source (R₃ is H) or an alkylating (R₃ is lower alkyl) or acylating (R₃ is lower acyl) reagent;

or (d), particularly in cases where R₄ is perfluoroalkyl, reacting a compound of general formula (9) with a silyl derivative of general formula R₄SiMe₃.

Alternatively, the compound of formula (1) wherein A is

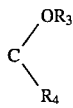

and R₃ is H may be first obtained as above and then converted into the compound wherein R₃ is lower alkyl or lower acyl.

The processes (a), (b) or (c) can be achieved for example, by reacting together a ketone of structure (5) or (7) or (9) with a preformed organometallic derivative (6) or (8) or R₄M respectively in a suitable anhydrous solvent such as diethylether, tetrahydrofuran or hexane or mixtures thereof. Said reaction should be conducted at a suitable temperature, normally between −100° C. and +50° C. and preferably under an inert atmosphere, normally nitrogen or argon. In a specific variation, a solution of the ketone of structure (5) or (7) or (9) in anhydrous diethylether or tetrahydrofuran is added dropwise to the organometallic derivative (6) or (S) or R₄M respectively in anhydrous diethylether or tetrahydrofuran or hexane or mixtures thereof at a temperature of about −50° C. to −78° C. and under an atmosphere of nitrogen. After a suitable period of time the reaction mixture is allowed to warm to room temperature and then quenched by the addition of water or a lower alcohol. The required product (1) wherein A is

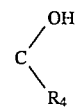

may then be isolated and purified and characterised using standard techniques.

The process (d) can be achieved, for example, by treating a solution of the ketone (9) and the silyl derivative R₄SiMe₃ in a suitable anhydrous solvent such as diethylether or tetrahydrofuran with tetrabutylammonium fluoride. Said reaction should be conducted at a suitable temperature, normally between −100° C. and +50° C. and preferably under an inert atmosphere, normally nitrogen or argon. After a suitable period of time the reaction mixture is allowed to come to room temperature and is then treated with 6M hydrochloric acid. The required product (1) wherein A is

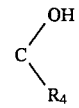

may then be isolated and purified and characterised using standard techniques.

Ketones of general formula (5) or (7) or (9) are either compounds which are commercially available or have been previously described in the literature, or compounds previously described in the literature, or compounds which can be prepared by the straightforward application of known methods.

Thus, the present invention also refers to some new intermediates, namely 4 or 5 acyl substituted compounds of the general formulas (5) and (9), respectively:

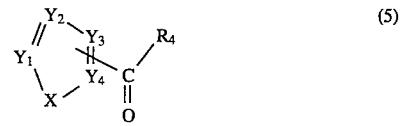

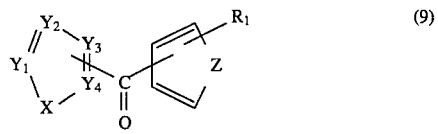

wherein

X is O, S or Se;

Y₁ is C—H, C-lower alkyl or C—CF₃;

Y₂ is N;

either Y₃ or Y₄ is CR₂ and the acyl group is attached to the other of these positions;

$R_4$ is $C_2$ to $C_6$ alkyl or perfluoroalkyl;

and $R_1$, $R_2$ and Z are as defined above
with the provisos that when X is O, the acyl group is not attached to $Y_3$ and that the following four compounds are excluded:

ethyl 4-thiazolyl ketone;

tert-butyl 5-thiazolyl ketone;

tert-butyl 5-oxazolyl ketone;

tert-butyl 4-tert-butyl-2-methyl-5-oxazolyl ketone.

In the organometallic derivatives of general formula (6) or (8) or $R_4M$, M represents a metallic residue such as Li or Mg-halogen. Such compounds are either commercially available or have been previously described in the literature, or can be prepared by the straightforward application of known methods of organometallic chemistry.

Silyl derivatives of formula $R_4SiMe_3$ are either commercially available, for example, $CF_3SiMe_3$, or have been previously described in the literature or can be prepared by the straightforward application of known methods.

Compounds of formula (1) wherein A is

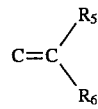

may be prepared by (a) elimination of $HWR_3$ from a compound of formula (1) wherein A is

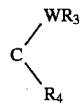

or (b) by using a compound of general formula (9) as the substrate for a standard alkene forming reaction such as the Wittig reaction, the Peterson reaction or the McMurry reaction.

The process (a) can be achieved, for example, by treatment of a solution of a compound of formula (1) wherein A is

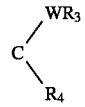

in a suitable inert solvent with an acid or a base or a reagent such as thionyl chloride or phosphorus oxychloride. Said reaction should be conducted at a suitable temperature, normally between −20° C. and the reflux temperature of the solvent. In a preferred variation, a solution of a compound of formula (1) wherein A is

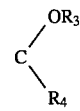

in a solvent such as dichloromethane or chloroform at 0° C. to 10° C. is treated with an acid such as anhydrous hydrogen chloride or p-tol enesulphonic acid, or with thionyl chloride. The reaction is then allowed to proceed at ambient temperature or above. The required product (1) wherein A is

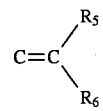

may then be isolated and purified and characterised using standard techniques.

Compounds of formula (1) wherein A is

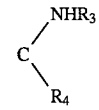

may be prepared by (a) using a compound of general formula (1) wherein A is

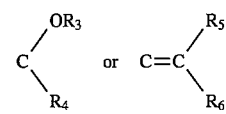

as the substrate for a Ritter reaction, or (b) by using a compound of general formula (1) wherein A is

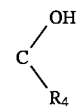

as the substrate for a Mitsunobu-type reaction or (c) reacting a compound of general formula (1) wherein A is

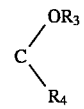

with trimethylsilylazide, $Me_3SiN_3$, in the presence of a Lewis acid such as boron trifluoride diethyletherate to give an azide of formula (1) wherein A is

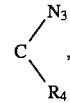

and then reducing said azide using, for example, hydrogen in the presence of a palladium or platinium catalyst.

Some compounds of general formula (1) contain an asymmetric centre and can thus exist in enantiomeric forms. These enantiomers may be separated using methods that will be well known to one skilled in the art. Such methods include, for example, (i) direct separation by means of chiral chromatography, for example, by HPLC using a chiral column;

or (ii) recrystallisation of the diastereomeric salts formed by reacting the base (1) with an optically active acid;

or (iii) derivatization of the compound of formula (1) by reaction with an optically active reagent, separation of the resultant diastereoisomeric derivatives by, for example, crystallisation or chromatography, followed by regeneration of the compound of formula (1).

Alternatively, compounds of formula (1) may be obtained directly in an optically active form by using a chemical or enzymatic based method of asymmetric synthesis.

Some compounds of general formula (1) wherein A is

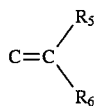

can exist as E and Z (trans and cis) isomers. Such isomers may be separated using standard techniques, for example, crystallisation or chromatography, that will be readily apparent to one skilled in the art.

Pharmacology

The neuroprotective properties of the compounds of formula (1) are exemplified by their ability to inhibit delayed neuronal death in the gerbil bilateral occlusion model of ischaemia.

Animals used were male Mongolian gerbils (60–80 g). Drugs were dissolved in isotonic saline containing dimethylsulphoxide.

Ischaemia was induced in the gerbils by 5 minute occlusion of both carotid arteries following the procedure described by R. Gill, A.C. Foster and G.N. Woodruff, J. Neuroscience. 1987, 7, 3343–3349. Body temperature was maintained at 37° C. throughout. Restoration of blood flow after occlusion was checked visually and the animals were allowed to survive for 4 days. The extent of neuronal degeneration in the hippocampus was then assessed. The test compounds were administered (i.p.) as a single dose 60 minutes following occlusion. No administration was made prior to the occlusion. The effectiveness of the compounds of formula (1) in decreasing damage to the CA1/CA2 hippocampal neurones in gerbils following ischaemic insult clearly illustrates the usefulness of these compounds in preventing neurodegeneration. These compounds are therefore expected to be of value in the treatment of acute and chronic neuropsychiatric disorders characterised by progressive processes that sooner or later lead to neuronal cell death and dysfunction.

Pharmaceutical Formulations

The administration in the novel method of treatment of this invention may conveniently be oral, rectal, topical or parenteral at a dosage level of, for example, about 0.01 to 1000 mg/kg, preferably about 1.0 to 500 mg/kg and especially about 5.0 to 200 mg/kg and maybe administered on a regimen of 1 to 4 doses or treatments per day. The dose will depend on the route of administration, preferred routes being oral or intravenous administration. It will be appreciated that the severity of the disease, the age of the patient and other factors normally considered by the attending physician will influence the individual regimen and dosage most appropriate for a particular patient.

The pharmaceutical formulations comprising the compound of this invention may conveniently be tablets, pills, capsules, syrups, powders or granules for oral administration; sterile parenteral solutions or suspensions for parenteral administration; suppositories for rectal administration; or suitable topical formulations. Conventional procedures for the selection and preparation of suitable pharmaceutical formulations are described, for example, in "Pharmaceuticals—The Science of Dosage Form Design", M. E. Aulton, Churchill Livingstone, 1988.

To produce pharmaceutical formulations containing a compound according to the present invention in the form of dosage units for oral application the active substance may be admixed with an adjuvant/a carrier e.g. lactose, saccharose, sorbitol, mannitol, starches such as potato starch, corn starch or amylopectin, cellulose derivatives, a binder such as gelatine or polyvinyl-pyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs my be added to these coatings in order to readily distinguish between tablets containing different active substances or different amounts of the active confounds.

For the preparation of soft gelatine capsules, the active substance may be admixed with e.g. a vegetable oil or polyethylene glycol. Hard gelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.02% to about 20% by weight of the active substance herein described, the balance being sugar and a mixture of ethanol, water, glycerol and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may involve the use of surface acting agents to improve solubility. They may conveniently be provided in various dosage unit ampoules.

The necessary starting materials for all Preparations and Examples were purchased commercially except as follows:

4-methyl-5-oxazolecarbonyl chloride (Indian J. Chem., Sect. B. 1985, 24B, 535–8);

2,4-dimethyl-5-oxazolecarbonyl chloride (EP 154 132);

5-acetyl-4-methyloxazole (Chem. Ber., 1960, 93, 1998–2001);

5-acetyl-4-methylthiazole (J. Agr. Food Chem., 1974, 22, 264–9);

5-acetyl-2,4-dimethyloxazole (Chem. Bet., 1960, 93, 1998–2001);

4-acetyl-2,5-dimethyloxazole (J. Am. Chem. Soc., 1975, 97, 6484–6491);

5-acetyl-3-methylisoxazole and 3-acetyl-5-methylisoxazole (J. Org. Chem., 1989, 54, 2646–2650).

PREPARATION 1

N-Methoxy-N-methyl-4-methyl-5-oxazolecarboxamide

4-Methyl-5-oxazolecarbonyl chloride (15 g) and N,O-dimethylhydroxylamine hydrochloride (11 g) in dry chloroform (100 ml) were cooled to 0° C. and dry pyridine (28.5 g) was added. The mixture was allowed to warm to room temperature. After 30 minutes aqueous sodium hydrogen carbonate was added and the organic layer separated. The aqueous layer was extracted with dichloromethane. The combined organic layers were washed, dried and evaporated. The residue was purified by flash chromatography to yield the title compound as a white solid. M.p. 59°–60° C.

$^1$H Nmr (CDCl$_3$) 2.5, 3.34 and 3.82 (each 3H, s) and 7.86 (1H, s) ppm.

Found: C, 49.0; H, 5.6; N, 16.4. C$_7$H$_{10}$N$_2$O$_3$ requires C, 49.4; H, 5.9; N, 16.54%

PREPARATION 2

N-Methoxy-N-methyl-2,4-dimethyl-5-oxazolecarboxamide

Starting with 2,4-dimethyl-5-oxazolecarbonyl chloride and following the general method of Preparation 1, the title compound was obtained as a waxy solid.

$^1$H Nmr (CDCl$_3$) 2.42, 2.5, 3.32 and 3.8 (each 3H, s) ppm.

PREPARATION 3

3-Furyl 4-Methyl-5-oxazolyl Ketone

3-Bromofuran (2.5 g) in dry diethylether was stirred and cooled to –70° C. under an atmosphere of dry nitrogen and n-butyllithium (2.5M solution in hexane, 6.8 ml) was added dropwise. After 30 minutes, N-methoxy-N-methyl-4-methyl-5-oxazolecarboxamide (2.89 g) in dry diethylether was added dropwise. After a further 30 minutes the mixture was allowed to warm to room temperature. Ethanol (5 ml) was added followed by saturated aqueous sodium chloride. The mixture was extracted with dichloromethane and the material thus obtained was purified by flash chromatography to give the title compound. M.p. 82°–83.5° C.

$^1$H Nmr (CDCl$_3$) 2.62 (3H, s), 7.01, 7.52, 7.95 and 8.42 (each 1H) ppm.

Found: C, 60.8; H, 4.4; N, 8.0. C$_9$H$_7$NO$_3$ requires C, 61.0; H, 4.0; N, 7.94%

PREPARATION 4

5-Acetyl-2-ethyl-4-methyloxazole

3-Chloropentane-2,4-dione (46.5 g), propionamide (50 g) and propionic acid (151 g) were heated at 145° C. for 5 hours. The mixture was cooled to room temperature, then basified to pH 10 using 10M aqueous sodium hydroxide, and extracted with dichloromethane. The combined extracts were washed with brine, dried and the solvent removed to leave a brown oil which was purified by vacuum distillation, b.p. 70° C. at 2 mbar.

$^{13}$C Nmr (CDCl$_3$) 10.6, 13.4, 21.6, 27.2, 144.7, 145.0, 166.4 and 187.2 ppm.

PREPARATION 5

4-Methyl-5-propionyloxazole

N-Methoxy-N-methyl-4-methyl-5-oxazolecarboxamide (5 g) in dry tetrahydrofuran at –40° C. was stirred under a nitrogen atmosphere and ethylmagnesium bromide (1M solution in tetrahydrofuran, 35 ml) was added dropwise. After 30 minutes the mixture was allowed to warm to room temperature and then stirred for a further 1 hour. Aqueous sodium hydrogen carbonate was added, the organic layer was separated and the aqueous layer was extracted with diethylether. The material thus obtained was purified by flash chromatography to yield a pale yellow liquid which solidified on cooling.

$^1$H Nmr (CDCl$_3$) 1.22 (3H, t), 2.53 (3H, s), 2.85 (2H, q) and 7.84 (1H, s) ppm.

PREPARATION 6

2,4-Dimethyl-5-propionyloxazole

Following the general method of Preparation 5 but starting with N-methoxy-N-methyl-2,4-dimethyl-5-oxazolecarboxamide, the title compound was obtained as a low-melting solid.

$^1$H Nmr (CDCl$_3$) 1.21 (3H, t), 2.48 and 2.52 (each 3H, s) and 2.84 (2H, q) ppm.

PREPARATION 7

4-Methyl-2-trimethylsilylthiazole n-Butyllithium (2.5M solution in hexane, 1.1 equivalents) was added dropwise to a solution of 4-methylthiazole (1.0 equivalent) in dry diethyl ether at –70° C. under an atmosphere of dry nitrogen. After 30 minutes, trimethylsilylchloride (1.0 equivalent) was added dropwise. The mixture was allowed to warm to room temperature and was then quenched by the addition of saturated aqueous sodium hydrogen carbonate. Work-up in the normal fashion and vacuum distillation then gave the title compound. B.p. 42° C. at 1 mm Hg.

PREPARATION 8

2,4-Dimethyl-5-oxazolyl 3-Furyl Ketone

Following the method of Preparation 3 but using N-methoxy-N-methyl-2,4-dimethyl-5-oxazolecarboxamide, the title compound was prepared. M.p. 73.5°–74.5° C.

Found: C, 62.6; H, 4.7; N, 7.45. C$_{10}$H$_9$NO$_3$ requires C, 62.8; H, 4.75; N, 7.3%

PREPARATION 9

Cyclopropyl 4-Methyl-5-oxazolyl Ketone

Following the method of Preparation 3 but using cyclopropyl magnesium bromide, the title compound was obtained.

$^1$H Nmr (CDCl$_3$) 1.06 and 1.25 (each 2H, m), 2.53 (3H, s), 2.65 (1H, m) and 7.91 (1H, s) ppm.

PREPARATION 10 t-Butyl 2,4-Dimethyl-5-oxazolyl Ketone

Starting with N-methoxy-N-methyl-2,4-dimethyl-5-oxazolecarboxamide and t-butyllithium and following the general method of Preparation 3, the title compound was prepared.

$^{13}$C Nmr (CDCl$_3$) 13.7, 13.9, 26.0, 43.3, 144.2, 147.1, 160.8 and 195.1 ppm.

PREPARATION 11

2,4-Dimethyl-5-oxazolyl 2-Propyl Ketone

Starting with N-methoxy-N-methyl-2,4-dimethyl-5-oxazolecarboxamide and 2-propyl magnesium chloride and following the general method of Preparation 3, the title compound was obtained.

$^{13}$C Nmr (CDCl$_3$) 13.3, 13.9, 17.9, 36.8, 144.3, 145.3, 161.6 and 193.8 ppm.

PREPARATION 12

3-Trifluoroacetylfuran

3-Bromofuran (20 g) was added to a solution of n-butyllithium (2.5M in hexanes, 60 ml) in diethyl ether (200 ml) at −70° C. After 30 minutes, ethyl trifluoroacetate (28.6 g) was added slowly. After a further 1 hour the mixture was allowed to warm to room temperature and was then left to stir overnight. 1M Hydrochloric acid (100 ml) was added and the mixture stirred for 5 minutes. The organic layer was separated, washed, dried and evaporated. The residue was distilled to give the title compound. B.p. 118° C.

$^{13}$C Nmr (CDCl$_3$) 109.0, 116.2 (q, J 290 Hz), 121.0, 144.9, 150.6 and 175.5 (q, J 37 Hz) ppm.

PREPARATION 13

3-Trifluoroacetylthiophene

The title compound was prepared following the method of Preparation 12 but using 3-bromothiophene. B.p. 48° C. at 10 mBar.

$^{13}$C Nmr (CDCl$_3$) 116.8 (q, J 290 Hz), 127.4, 127.9, 134.5, 137.3 and 174.8 (q, J 37 Hz) ppm.

PREPARATION 14

5-Acetyl-2-amino-4-trifluoromethylthiazole

Hydroxy(tosyloxy)iodobenzene (78.5 g) was added to a solution of 1,1,1-trifluoropentane-2,4-dione in acetonitrile (500 ml). The mixture was heated under reflux for 45 minutes, then cooled, and thiourea (15.2 g) was added. The mixture was heated under reflux for 4 hours and then left to stand overnight. Evaporation and crystallisation of the residue from dichloromethane gave the title compound.

$^{13}$C Nmr (d$_6$-DMSO) 29.5, 120.1, (q, J 270 Hz), 125.5, 141.1, (q, J 35Hz), 170.3 and 187.2 ppm.

PREPARATION 15

5-Acetyl-4-trifluoromethylthiazole

The product from Preparation 14 (7 g) was added to a mixture of nitric acid (69%, 10 ml) and phosphoric acid (85%, 48 ml). The suspension was stirred and cooled to −20° C. and sodium nitrite (3.6 g) in water (30 ml) was added dropwise. After a further 30 minutes at −20° C., hypophosphorous acid (50%, 19.5 ml) was added dropwise. After 15 minutes the mixture was allowed to warm to 0° C. After 1 hour was basified using 40% aqueous sodium hydroxide and extracted with dichloromethane. The extracts were washed, dried and evaporated and the residue was purified by flash chromatography to give the title compound.

$^{13}$C Nmr (CDCl$_3$) 30.3, 120.2 (q, J 270 Hz), 140.2, 144.0 (q, J 38 Hz), 155.6 and 189.2 ppm.

PREPARATION 16

4-Bromo-1,3,5-trimethylpyrazole

4-Bromo-3,5-dimethylpyrazole (10 g) in dry dimethylformamide (50 ml) was added to a stirred suspension of sodium hydride (1.8 g) in dry dimethylformamide at 0° C. When the evolution of hydrogen was complete, iodomethane (8.9 g) was added dropwise. The mixture was allowed to warm to room temperature and after 30 minutes saturated aqueous sodium hydrogen carbonate (5 ml) was added. Following evaporation under high vacuum, the residue was purified by column chromatography to give the title compound.

$^1$H Nmr (CDCl$_3$) 2.2, 2.22 and 3.73 (each 3H, s) ppm.

PREPARATION 17

4-Methyl-2-trifluoroacetyloxazole

1-Trifluoroacetylimidazole (10 g) was added dropwise to 4-methyl-2-trimethylsilyloxazole (J. Chem. Soc., Chem. Commun., 1984, 258) (9.95 g) in diethyl ether (100 ml) at 0° C. under an atmosphere of dry nitrogen. The mixture was stirred overnight at room temperature. Water was added and the organic layer was separated, washed, dried and evaporated. Flash chromatography gave the title compound.

$^{13}$C Nmr (d$_6$-DMSO) (as hydrate) 11.0, 89.5, (q, J 33 Hz), 122.3 (q, J 287 Hz), 136.0, 136.1 and 158.6 ppm.

PREPARATION 18

5-Methoxymethyl-4-methylthiazole

4-Methyl-5-thiazolecarbaldehyde (J. Amer. Chem. Soc., 1982, 104, 4934–4943) was reduced using aluminium isopropoxide in 2-propanol. The resulting alcohol was treated with sodium hydride in dimethoxyethane and iodomethane was added. Distillation gave the title compound.

$^{13}$C Nmr (CDCl$_3$) 14.2, 57.0, 64.9, 127.2, 149.9 and 150.5 ppm.

EXAMPLE 1

1-(3-Furyl)-1-(4-methyl-5-oxazolyl)ethanol a) 3-Bromofuran (7.6 g) in dry tetrahydrofuran (25 ml) at −70° C. under a nitrogen atmosphere was treated dropwise with n-butyllithium (2.5M solution in hexane, 20.8 ml). After 30 minutes, 5-acetyl-4-methyloxazole (5 g) was added dropwise. After a further 30 minutes at −70° C., the reaction mixture was allowed to warm to room temperature and then stirred for 30 minutes. Ethanol (12 ml) was added and the reaction mixture was then poured into saturated aqueous sodium chloride and extracted with dichloromethane. The product thus obtained was purified by chromatography on silica gel or neutral alumina. Crystallisation from diethylether then gave 1-(3-furyl)-1-(4-methyl-5-oxazolyl)ethanol as a white solid, m.p. 102°–103° C.

$^1$H Nmr (CDCl$_3$) 1.9 (3H, s), 2.1 (3H, s), 6.36 (1H, q), 7.37–7.41 (2H, m) and 7.67 (1H, s) ppm.

$^{13}$C Nmr (CDCl$_3$) 12.4, 28.9, 68.4, 108.8, 130.7, 131.1, 138.8, 143.5, 148.4 and 149.0 ppm.

Found: C, 62.3; H, 5.7; N, 7.3. C$_{10}$H$_{11}$NO$_3$ requires C, 62.2; H, 5.7; N, 7.25% b) 3-Furyl 4-methyl-5-oxazolyl ketone (1 g) in dry diethylether (15 ml) at −70° C. under a nitrogen atmosphere was treated dropwise with methyllithium (1.5M solution in diethylether, 4.1 ml). After 45 minutes the reaction mixture was allowed to warm to room temperature and ethanol (2 ml) was added. The mixture was poured into saturated aqueous sodium chloride and extracted with dichloromethane. Chromatography and crystallisation then gave 1-(3-furyl)-1-(4-methyl-5-oxazolyl)ethanol identical to the material obtained in (a) above.

EXAMPLE 2

1-(4-Methyl-5-oxazolyl)-1-(3-thienyl)ethanol

3-Bromothiophene (4.23 g) in diethylether (10 ml) was added dropwise to n-butyllithium (2.5M solution in hexane, 10.4 ml) in dry diethylether (20 ml) at −70° C. under a nitrogen atmosphere. After 3 hours 5-acetyl-4-methyloxazole (2.5 g) in diethylether (10 ml) was added dropwise. After a further 2.5 hours at −70° C., the mixture was allowed to warm to room temperature and then left overnight. The mixture was poured into water and extracted with ether. The product thus obtained was crystallised from diethylether to give 1-(4-methyl-5-oxazolyl)-1-(3-thienyl)ethanol, m.p. 87°–89° C.

$^1$H Nmr (CDCl$_3$) 1.93 (3H, s), 2.0 (3H, s), 7.05 (1H, m), 7.2–7.35 (2H, m) and 7.66 (1H, s) ppm.

$^{13}$C Nmr (CDCl$_3$) 12.2, 29.3, 71.0, 120.8, 125.9, 126.3, 131.0 146.9, 148.5 and 149.3 ppm.

Found: C, 57.2; H, 5.3; N, 6.6; S, 15.1. C$_{10}$H$_{11}$NO$_2$S requires C, 57.4; H, 5.3; N, 6.7; S, 15.3%

EXAMPLE 3

1-(4-Methyl-5-oxazolyl)-1-(2-thienyl)ethanol

Thiophene (3.36 g) in dry tetrahydrofuran (20 ml) was stirred and cooled to −40° C. under a dry nitrogen atmosphere and n-butyllithium (2.5M solution in hexane, 16 ml) was added dropwise. The mixture was allowed to warm to −20° C. and then after 1 hour was cooled to −70° C. 5-Acetyl-4-methyloxazole (5 g) in dry tetrahydrofuran (15 ml) was added dropwise. After a further 1 hour the mixture was allowed to warm the room temperature and was stirred for a further 2 hours. Aqueous sodium hydrogen carbonate was added and the mixture was extracted with diethylether. The material thus obtained was purified by flaon chromatography to give the title compound. M.p. 84°–85° C.

$^1$H Nmr (CDCl$_3$) 2.04 and 2.1 (each 3H, s), 2.87 (1H, br s), 6.96 (2H, m), 7.29 (1H,m) and 7.72 (1H, s) ppm.

Found: C, 57.1; H, 5.2; N, 6.5. C$_{10}$H$_{11}$NO$_2$S requires C, 57.4; H, 5.3; N, 6.7%

EXAMPLE 4

1-(3-Furyl)-1-(4-methyl-5-thiazolyl)ethanol

3-Bromofuran (6.8 g) in diethylether (15 ml) was added dropwise to n-butyllithium (2.5M solution in hexane, 18.4 ml) in diethylether (20 ml) at −70° C. under a nitrogen atmosphere. After 1 hour, 5-acetyl-4-methylthiazole (5 g) in diethylether (15 ml) was added dropwise. After a further 3 hours at −70° C., the mixture was allowed to warm to room temperature and was then left overnight. The mixture was poured into water and extracted with diethylether. The product thus obtained was crystallised from diethylether, m.p. 102°–104° C.

$^1$H Nmr (CDCl$_3$) 1.94 (3H, s), 2.25 (3H, s), 6.35 (1H, m), 7.35 (2H, m) and 8.47 (1H, s) ppm.

$^{13}$C Nmr (CDCl$_3$) 15.9, 30.2, 69.2, 109.0, 131.9, 139.0, 139.7, 143.5, 147.3 and 149.0 ppm.

Found: C, 57.4; H, 5.4; N, 6.7. C$_{10}$H$_{11}$NO$_2$S requires C, 57.4; H, 5.3; N, 6.7%

EXAMPLE 5

1-(2,4-Dimethyl-5-oxazolyl)-1-(3-furyl)ethanol

The title compound was prepared following the general method of Example 4 but starting with 5-acetyl-2,4dimethyloxazole. M.p. 93°–95° C.

$^1$H Nmr (CDCl$_3$) 1.88 (3H, s), 2.0 (3H, s), 2.35 (3H, s), 3.5 (1H, s), 6.36 (1H, m) and 7.4 (2H, m) ppm.

$^{13}$C Nmr (CDCl$_3$) 12.3, 13.6, 29.0, 68.3, 108.9, 130.8, 131.4, 138., 143.3, 148.4 and 158.8 ppm.

Found: C, 63.8; H, 6.4; N, 6.7. C$_{11}$H$_{13}$NO$_3$ requires C, 63.75; H, 6.3; N, 6.8%

EXAMPLE 6

1-(2,4-Dimethyl-5-thiazolyl)-1-(3-furyl)ethanol

The title compound was prepared following the general method of Example 4 but starting with 5-acetyl-2,4-dimethylthiazole. M.p. 104°–105° C.

$^1$H Nmr (CDCl$_3$) 1.9 (3H, s), 2.15 (3H, s), 2.55 (3H, s), 3.85 (1H, s), 6.33 (1H, m) and 7.38 (2H, m) ppm.

$^{13}$C Nmr (CDCl$_3$) 15.95, 18.5, 30.6, 69.3, 108.95, 132.1, 138.3, 138.9, 143.4, 146.25 and 161.9 ppm.

Found: C, 59.2; H, 5.9; N, 6.1; S, 14.2. C$_{11}$H$_{13}$NO$_2$S requires C, 59.2; H, 5.9; N, 6.3; S, 14.4%

EXAMPLE 7

1-(4-Methyl-5-thiazolyl)-1-(3-thienyl)ethanol

The title compound was prepared following the general method of Example 4 but using 3-bromothiophene. M.p. 149°–151° C.

$^1$H Nmr (d$_6$-DMSO) 1.96 (3H, s), 2.16 (3H, s), 6.2 (1H, s), 7.08 (1H, m), 7.5 (2H, m) and 8.8 (1H, s) ppm.

$^{13}$C Nmr (d$_6$-DMSO) 15.8, 30.5, 70.4, 120.6, 125.95, 126.8, 140.8, 146.5, 148.8 and 149.2 ppm.

Found: C, 52.9; H, 5.0; N, 6.0. C$_{10}$H$_{11}$NOS$_2$ requires C, 53.3; H, 4.9; N, 6.2%

The above compound in dry tetrahydrofuran was treated with dry hydrogen chloride in diethylether to give 1-(4-methyl-5-thiazolyl)-1-(3-thienyl)ethanol hydrochloride. M.p. 111°–112° C.

$^1$H Nmr (d$_6$-DMSO) 2.04 and 2.26 (each 3H, s), 6.0 (br s), 7.16 (1H, m), 7.62 (2H, m) and 9.5 (1H, s) ppm.

EXAMPLE 8

1-(2,4-Dimethyl-5-oxazolyl)-1-(3-thienyl)ethanol

Starting with 3-bromothiophene and 5-acetyl-2,4-dimethyloxazole dimethyloxazole and following the general method of Example 4 the title compound was prepared. M.p. 132°–133° C.

$^1$H Nmr (CDCl$_3$) 1.86, 1.92 and 2.35 (each 3H, s), 3.23 (1H, br s) and 7.05, 7.27 and 7.31 (each 1H, m) ppm.

$^{13}$C Nmr (CDCl$_3$) 12.2, 13.8, 29.4, 71.0, 120.8, 126.1, 126.2, 131.3, 147.1, 148.6 and 158.9 ppm.

EXAMPLE 9

1-(2-Ethyl-4-methyl-5-oxazolyl)-1-(3-thienyl)ethanol

Starting with 3-bromothiophene and 5-acetyl-2-ethyl-4-methyloxazole and following the general method of Example 4 the title compound was prepared. M.p. 77.5°–79° C.

$^1$H Nmr (CDCl$_3$) 1.23 (3H, t), 1.77 (3H, s), 1.9 (3H, s) 2.6 (2H, q), 5.15 (1H, s), 7.0 (1H, m) and 7.23 (2H, m) ppm.

$^{13}$C Nmr (CDCl$_3$) 10.7, 11.5, 20.9, 29.0, 70.1, 120.1, 125.4, 125.8, 130.3, 147.3, 148.5 and 162.6 ppm.

EXAMPLE 10

1-(3-Furyl)-1-(4-methyl-5-oxazolyl)propanol

Starting with 3-bromofuran and 4-methyl-5propionyloxazole and following the general method of Example 4 the title compound was prepared.

$^1$H Nmr (CDCl$_3$) 0.92 (3H, t), 2.0–2.3 (2H, m), 2.15 (3H, s), 6.36 (1H, m), 7.4 (2H, m) and 7.66 (1H, s) ppm.

EXAMPLE 11

1-(2-Ethyl-4-methyl-5-oxazolyl)-1-(3-furyl)ethanol

Starting with 3-bromofuran and 5-acetyl-2-ethyl-4methyloxazole and following the general method of Example 4 the title compound was prepared.

$^1$H Nmr (CDCl$_3$) 1.32 (3H, t), 1.88 and 2.04 (each 3H, s), 2.73 (2H, q), 2.82, (1H, br s), 6.38 (1H, m) and 7.4 (2H, m) ppm.

$^{13}$C Nmr (CDCl$_3$) 11.1, 12.5, 21.5, 29.1, 68.6, 108.9, 130.9, 131.4, 138.9, 143.4, 148.0 and 163.2 ppm.

EXAMPLE 12

1-(2,4-Dimethyl-5-oxazolyl)-1-(3-thienyl)propanol

Starting with 3-bromothiophene and 2,4-dimethyl-5propionyloxazole and following the general method of Example 4 the title compound was prepared. Purification by preparative HPLC gave a white solid. M.p. 81°–83° C.

$^{13}$C Nmr (CDCl$_3$) 8.0, 12.4, 13.8, 35.1, 74.5, 124.0, 124.9, 126.8, 132.5, 147.7, 149.9 and 159.0 ppm.

Found: C, 60.6; H, 6.2; N, 5.7. C$_{12}$H$_{15}$NO$_2$S requires C, 60.7; H, 6.4; N, 5.9%

EXAMPLE 13

1-(2,5-Dimethyl-4-oxazolyl)-1-(3-furyl)ethanol

Starting with 3-bromofuran and 4-acetyl-2,5dimethyloxazole and following the general method of Example 4 the title compound was prepared.

$^1$H Nmr (CDCl$_3$) 1.8, 2.12 and 2.34 (each 3H, s), 3.6 (1H, br s), 6.38 (1H, m) and 7.32 (2H, m) ppm.

$^{13}$C Nmr (CDCl$_3$) 11.1, 13.6, 29.2, 68.1, 109.1, 132.1, 138.7, 142.4, 143.1 and 158.2 ppm.

EXAMPLE 14

1-(2,5-Dimethyl-4-oxazolyl)-1-(3-thienyl)ethanol

Starting with 3-bromothiophene and 4-acetyl-2,5dimethyloxazole and following the general method of Example 4 the title compound was prepared. M.p. 83°–84° C.

$^1$H Nmr (CDCl$_3$) 1.88, 1.98 and 2.35 (each 3H, s), 3.85 (1H, br s), 7.08 (1H, m) and 7.26 (2H, m) ppm.

$^{13}$C Nmr (CDCl$_3$) 10.8, 13.5, 29.6, 70.6, 120.4, 125.6, 126.4, 139.1, 142.5, 148.2 and 158.2 ppm.

EXAMPLE 15

1-(2,5-Dimethyl-3-furyl)-1-(4-methyl-5-thiazolyl)-ethanol

4-Methylthiazole (6.51 g) in dry tetrahydrofuran (50 ml) was stirred under an atmosphere of dry nitrogen and cooled to −70° C. and n-butyllithium (2.5M solution in hexane, 29 ml) was added dropwise. After 30 minutes trimethylsilylchloride (7.14 g) was added and the mixture was allowed to warm to room temperature. After 30 minutes the mixture was again cooled to −70° C. and n-butyllithium (2.5M solution in hexane, 29 ml) was added dropwise. After 30 minutes 3-acetyl-2,5-dimethylfuran (10 g) was added dropwise. The mixture was stirred at −70° C. for 1 hour and was then allowed to warm to room temperature. After 30 minutes, aqueous sodium hydrogen carbonate was added and the mixture was extracted with diethylether. The combined extracts were washed, dried and evaporated to give the title compound which was recrystallised from diethylether. M.p. 100.5°–101.5° C.

$^1$H Nmr (CDCl$_3$) 1.9, 2.06 and 2.24 (each 3H, s), 2.42 (1H, br s), 5.94 (1H, s) and 8.57 (1H, s) ppm.

Found: C, 60.6; H, 6.5; N, 5.9. C$_{12}$H$_{15}$NO$_2$S requires C, 60.7; H, 6.4; N, 5.94.

EXAMPLE 16

1-(2-Furyl)-1-(4-methyl-5-thiazolyl)ethanol

Starting with 4-methylthiazole and 2-acetylfuran and following the general method of Example 15 the title compound was prepared. M.p. 127°–128° C.

$^1$H Nmr (CDCl$_3$) 1.97 and 2.18 (each 3H, s), 3.3 (1H, br s), 6.32, 6.39 and 7.41 (each 1H, m) and 8.56 (1H, s) ppm.

Found: C, 57.3; H, 5.2; N, 6.6. C$_{10}$H$_{11}$NO$_2$S requires C, 57.4; H, 5.3; N, 6.7%

EXAMPLE 17

1-(4-Methyl-5-thiazolyl)-1-(2-thienyl)ethanol

Starting with 4-methylthiazole and 2-acetylthiophene and following the general method of Example 15 the title compound was prepared. M.p. 146.5°–147.5° C.

$^1$H Nmr (CDCl$_3$) 2.08 and 2.23 (each 3H, s), 3.14 (1H, br s), 6.96 (2H, m), 7.3 (1H, m) and 8.54 (1H, s) ppm.

Found: C, 53.0; H, 5.0; N, 6.0. C$_{10}$H$_{11}$NOS$_2$ requires C, 53.3; H, 4.9; N, 6.2%

The above compound in dry tetrahydrofuran was treated with dry hydrogen chloride in diethylether to give 1-(4-methyl-5-thiazolyl)-1-(2-thienyl)ethanol hydrochloride. M.p. 109.5°–110.5° C.

$^1$H Nmr (d$_6$-DMSO) 1.84 and 1.95 (each 3H, s), 3.87 (br s), 6.65, 6.73 and 7.13 (each 1H, m) and 8.84 (1H, s) ppm.

EXAMPLE 18

1-(5-Thiazolyl)-1-(3-thienyl)ethanol n-Butyllithium (2.5M solution in hexane, 5.6 ml) in diethylether (25 ml) was stirred at −70° C. under a nitrogen atmosphere and 2-trimethylsilylthiazole (2 g) in diethylether (25 ml) was added dropwise. After 30 minutes 3-acetylthiophene (1.93 g) in diethylether (25 ml) was added dropwise. After a further 45 minutes the mixture was allowed to warm to room temperature and then left to stir for a further 1 hour. Saturated aqueous sodium hydrogen carbonate was added and the organic layer was separated. The aqueous layer was extracted with diethylether. The organic layers were combined, washed, dried and evaporated and the residue was purified by flash chromatography to give the title compound as an oil.

$^1$H Nmr (CDCl$_3$) 2.02 (3H, s), 3.82 (1H, br s), 7.07 (1H, m), 7.28 (2H, m), 7.56 (1H, s) and 8.63 (1H, s) ppm.

$^{13}$C Nmr (CDCl$_3$) 32.3, 71.8, 120.8, 126.0, 126.4, 139.3, 147.9, 148.3 and 152.9 ppm.

EXAMPLE 19

1-(3-Furyl)-1-(4-methyl-5-oxazolyl)ethene 1-(3-Furyl)-1-(4-methyl-5-oxazolyl)ethanol (900 mg) in dry chloroform was treated with 1M anhydrous hydrogen chloride in diethylether (1.1 equivalents). After 10 minutes at room temperature, aqueous sodium hydrogen carbonate was added and the mixture was extracted with dichloromethane. The material thus obtained was purified by flash chromatography to give the title compound as an almost colourless liquid.

$^1$H Nmr (CDCl$_3$) 2.22 (3H, s), 5.42 and 5.59 (each 1H, s), 6.55 and 7.44 (each 1H, m) and 7.52 and 7.81 (each 1H, s) ppm.

$^{13}$C Nmr (CDCl$_3$) 13.0, 109.2, 115.0, 123.9, 128.1, 133.2, 140.9, 143.2, 145.4 and 148.9 ppm.

EXAMPLE 20

1-(3-Furyl)-1-(4-methyl-5-oxazolyl)-1-propene

Starting from 1-(3-furyl)-1-(4-methyl-5-oxazolyl)propanol and following the method of Example 19 the title compound was obtained as a mixture of E and Z isomers.

$^1$H Nmr (CDCl$_3$) 1.8 and 1.92 (total 3H, d), 2.02 and 2.12 (total 3H, s), 6.1–6.3 (total 1H, m), 6.37 and 6.5 (total 1H, m), 7.18 and 7.43 (total 1H, s), 7.38 and 7.5 (total 1H, m) and 7.74 and 7.89 (total 1H, s) ppm.

EXAMPLE 21

1-(2,4-Dimethyl-5-oxazolyl)-1-(3-furyl)ethene Hydrochloride 1-(2,4-Dimethyl-5-oxazolyl)-1-(3-furyl)-1-methoxyethane (790 mg) in dry diethylether was treated with 1M anhydrous hydrogen chloride in diethylether (1.2 equivalents). The title compound was obtained as a white solid which was filtered off, washed and dried. M.p. 128.5°–130° C.

$^{13}$C Nmr (d$_6$-DMSO) 12.7, 13.7, 109.5, 114.8, 123.8, 127.8, 132.7, 141.5, 144.0, 144.6 and 159.7 ppm.

Found: C, 58.3; H, 5.3; N, 5.9. C$_{11}$H$_{11}$NO$_2$HCl requires C, 58.5; H, 5.4; N, 6.2%

EXAMPLE 22

1-(2-Furyl)-1-(4-methyl-5-oxazolyl)ethanol

5-Acetyl-4-methyloxazole (4 g) in dry diethylether was added dropwise to a stirred solution of 2-lithiofuran (1 equivalent) in diethylether at −20° C. The mixture was allowed to warm to room temperature and was then left overnight. Work-up and flash chromatography then gave the title compound as a white solid, m.p. 73°–75° C.

$^1$H Nmr (CDCl$_3$) 1.93 and 1.95 (each 3H, s), 2.92 (1H, s), 6.30 (1H, m), 6.38 (1H, m), 7.41 and 7.71 (each 1H, s) ppm.

EXAMPLE 23

1-(2,4-Dimethyl-5-thiazolyl)-1-(3-pyridyl)ethanol

5-Acetyl-2,4-dimethylthiazole (2.5 g) in dry diethylether (10 ml) was added dropwise to a stirred solution of 3-lithiopyridine (from 3.5 g 3-bromopyridine) in diethylether at −70° C. After 3 hours the mixture was allowed to warm to room temperature. After a further 1 hour, aqueous sodium hydrogen carbonate was added and the organic layer was separated. The aqueous layer was extracted with diethylether. The material obtained from the combined organic layers was purified by flash chromatography to give the title compound, m.p. 107.5°–109° C.

$^{13}$C Nmr (CDCl$_3$) 16.3, 18.7, 32.7, 71.9, 123.1, 133.5, 137.9, 142.4, 146.9, 148.0 and 162.2 ppm.

EXAMPLE 24

1-(2,4-Dimethyl-5-thiazolyl)-1-(2-pyridyl)ethanol

Using the general method of Example 23 but using 2-lithiopyridine, the title compound was obtained. M.p. 104°–105° C.

$^{13}$C Nmr (CDCl$_3$) 16.2, 18.8, 31.9, 72.5, 120.1, 122.4, 136.9, 137.2, 147.3, 148.6, 161.8 and 163.5 ppm.

EXAMPLE 25

1-(3,5-Dimethyl-4-isoxazolyl)-1-(3-furyl)ethanol

The title compound was prepared following the general method of Example 4 but starting with 4-acetyl-3,5-dimethylisoxazole (J.Am. Chem. Soc., 1975, 97, 6484–6491). M.p. 88°–90° C.

$^1$H Nmr (CDCl$_3$) 1.83, 2.11 and 2.33 (each 3H, s), 6.33 and 7.38 (each 1H, dd) and 7.42 (1H t) ppm.

EXAMPLE 26

1-(3,5-Dimethyl-4-isoxazolyl)-1-(3-thienyl)ethanol

The title compound was prepared following the general method of Example 4 but starting with 4-acetyl-3,5-dimethylisoxazole and 3-bromothiophene. M.p. 93.5°–95° C.

$^{13}$C Nmr (CDCl$_3$) 11.8, 12.7, 30.3, 70.1, 119.3, 120.8, 126.4, 126.5, 148.4, 158.9 and 164.8 ppm.

EXAMPLE 27

1-(2,4-Dimethyl-5-oxazolyl)-1-(3-furyl)ethyl Methyl Ether 1-(3-Furyl)-1-(2,4-dimethyl-5-oxazolyl)ethanol (2 g) in dry N,N-dimethylformamide (15 ml) was added to a stirred suspension of sodium hydride (80%, 300 mg) in dry N,N- dimethylformamide (10 ml) at 0° C. After 20 minutes, methyl iodide (1.5 g) was added dropwise. The mixture was allowed to warm to room temperature and after 30 minutes aqueous sodium hydrogen carbonate was added.

The mixture was then evaporated to dryness. The residue was treated with water and extracted with diethyl ether. The material thus obtained was purified by flash chromatography to give the title compound.

$^{13}$C Nmr (CDCl$_3$) 12.5, 13.8, 24.8, 50.9, 73.4, 109.3, 129.1, 132.7, 139.7, 143.1, 146.5 and 159.2 ppm.

EXAMPLE 28

1-(3-Furyl)-1-(4-methyl-5-oxazolyl)ethyl Methyl Ether

The title compound was prepared from 1-(3-furyl)-1-(4-methyl-5-oxazolyl)ethanol using the general method of Example 27.

$^1$H Nmr (CDCl$_3$) 1.81, 2.14 and 3.16 (each 3H, s), 6.32 and 7.74 (each 1H, br s) and 7.4 (1H, m)ppm.

EXAMPLE 29

1-(2-Thiazolyl)-1-(2-thienyl)ethanol n-Butyllithium (2.5M solution in hexanes, 13.4 ml) in dry diethyl ether (25 ml) was added dropwise to a stirred solution of 2-bromothiazole (5 g) in diethyl ether (50 ml) at −70° C. under an atmosphere of dry nitrogen. After 30 minutes, 2-acetylthiophene (3.85 g) in diethyl ether (25 ml) was added dropwise. After a further 1 hour the mixture was allowed to warm to room temperature and was left stirring overnight. Water was added.

The mixture was extracted with diethyl ether to give the title compound which was recrystallised from diethyl ether. M.p. 112°–113° C.

$^{13}$C Nmr (CDCl$_3$) 31.6, 74.8, 119.7, 124.1, 125.3, 126.8, 142.2, 150.5 and 177.1 ppm.

Following the general method of Example 29 and using the appropriate ketone, the compounds of Examples 30 to 35 were prepared.

EXAMPLE 30

1-(2-Furyl)-1-(2-thiazolyl)ethanol

M.p. 91°–92° C.

$^{13}$C Nmr (CDCl$_3$) 28.3, 72.7, 106.4, 110.3, 119.7, 142.1, 142.4, 156.6 and 175.4 ppm.

EXAMPLE 31

1-(2-Thiazolyl)-1-(3-thienyl)ethanol

M.p. 107°–108° C.

$^{13}$C Nmr (CDCl$_3$) 30.6, 74.6, 119.3, 121.1, 126.0, 126.1, 142.2, 147.3 and 177.8 ppm.

Hydrochloride, M.p. 120°–122° C.

$^{13}$C Nmr (d$_6$-DMSO) 30.2, 73.8, 120.2, 120.6, 125.9, 126.3, 141.1, 148.1 and 179.8 ppm.

EXAMPLE 32

1-(1-Methyl-2-pyrrolyl)-1-(2-thiazolyl)ethanol

M.p. 143°–144° C.

$^{13}$C Nmr (CDCl$_3$) 31.8, 35.4, 72.9, 106.3, 108.4, 119.9, 124.9, 134.2, 141.7 and 177.6 ppm.

EXAMPLE 33

1-(2-Benzofuranyl)-1-(2-thiazolyl)ethanol

M.p. 120°–121° C.

$^{13}$C Nmr (CDCl$_3$) 28.3, 73.2, 103.0, 111.3, 119.9, 121.3, 122.9, 124.5, 128.0, 142.1, 155.0, 159.3 and 174.7 ppm.

EXAMPLE 34

1-(2-Thiazolyl)-1-(3-thienyl)-2,2,2-trifluoroethanol

M.p. 96°–97° C.

Found: C, 40.6; H, 2.1; N, 5.2. C$_9$H$_6$F$_3$NOS$_2$ requires C, 40.75; H, 2.3; N, 5.3%

EXAMPLE 35

1-(3-Furyl)-1-(2-thiazolyl)-2,2,2-trifluoroethanol

M.p. 106°–107° C.

Found: C, 43.6; H, 2.3; N, 5.5. C$_9$H$_6$F$_3$NO$_2$S requires C, 43.4; H, 2.4; N, 5.6%

EXAMPLE 36

1-(4,5-Dimethyl-2-thiazolyl)-1-(2-thienyl)ethanol n-Butyllithium (2.5M solution in hexanes, 9.7 ml) was added dropwise to a stirred solution of 4,5-dimethylthiazole (2.5 g) in dry diethyl ether (30 ml) at −70° C. under an atmosphere of dry nitrogen. After 30 minutes, 2-acetylthiophene (3.1 g) in diethyl ether (20 ml) was added dropwise. After a further 1 hour the mixture was allowed to warm to room temperature and was then worked up in the normal fashion to yield the title compound.

M.p. 129°–130° C.

$^{13}$C Nmr (CDCl$_3$) 11.2, 14.6, 31.6, 74.3, 123.9, 124.9, 126.6, 127.2, 147.3, 151.2 and 171.7 ppm.

EXAMPLE 37

2-(4-Methyl-2-thiazolyl)-2-(2-thienyl)tetrahydrofuran

The title compound was prepared from 4-methylthiazole and 4-chloro-1-(2-thienyl)-1-butanone, using the general method of Example 36.

M.p. 59°–60° C.

$^{13}$C Nmr (CDCl$_3$) 17.4, 26.2, 41.2, 69.3, 86.2, 113.9, 124.2, 124.7, 126.8, 148,9, 153.1 and 175.6 ppm.

EXAMPLE 38

1-(4,5-Dimethyl-2-thiazolyl)-1-(3-thienyl)-2,2,2-trifluoroethanol

Starting with 3-(2,2,2-trifluoroacetyl)thiophene and using the general method of Example 36, the title compound was prepared.

M.p. 90°–92° C.

Found: C, 45.1; H, 3.2; N, 4.6. C$_{11}$H$_{10}$F$_3$NOS$_2$ requires C, 45.0; H, 3.4; N, 4.8%

Following the general method of Example 4 and using the appropriate ketone, the compounds of Examples 39 to 45 were prepared.

EXAMPLE 39

1-(3-Furyl)-1-(3-methyl-5-isoxazolyl)ethanol $^{13}$C Nmr (CDCl$_3$) 11.3, 28.4, 68.5, 101.2, 108.5, 130.2, 139.0, 143.3, 159.6 and 175.9 ppm.

EXAMPLE 40

1-(3-Furyl)-1-(5-methyl-3-isoxazolyl)ethanol

M.p. 49°–52° C.

$^{13}$C Nmr (CDCl$_3$) 12.2, 29.1, 68.7, 99.8, 108.7, 131.4, 138.8, 143.3, 169.3 and 169.6 ppm.

EXAMPLE 41

1-(3-Furyl)-1-(4-trifluoromethyl-5-thiazolyl)ethanol

M.p. 84°–85° C.

1H Nmr (CDCl$_3$) 1.95 (3H, s), 3.15 (1H, s), 6.27 (1H, m), 7.32 (2H, m) and 8.56 (1H, s) ppm.

EXAMPLE 42

1-Cyclopropyl-1-(3-furyl)-1-(4-methyl-5-oxazolyl)-methanol

M.p. 85°–86° C.

$^{13}$C Nmr (CDCl$_3$) 1.3, 1.5, 12.5, 20.4, 70.3, 109.3, 129.9, 131.5, 139.8, 143.2, 148.4 and 148.6 ppm.

EXAMPLE 43

2,2-Dimethyl-1-(2,4-dimethyl-5-oxazolyl)-1-(3-furyl)-1-propanol

M.p. 163°–164° C.

$^{13}$C Nmr (CDCl$_3$) 13.2, 13.8, 25.3, 40.2, 78.2, 111.0, 128.6, 132.9, 140.3, 141.8, 147.3 and 158.4 ppm.

EXAMPLE 44

1-(2,4-Dimethyl-5-oxazolyl)-1-(3-furyl)-2-methyl-1-propanol $^{13}$C Nmr (CDCl$_3$) 12.6, 13.8, 16.9, 36.9, 75.3, 109.3, 129.5, 132.0, 139.6, 142.8, 148.0 and 158.9 ppm.

EXAMPLE 45

1-(3-Furyl)-1-(4-methyl-2-oxazolyl)-2,2,2-trifluoroethanol $^1$H Nmr (CDCl$_3$) 2.18 (3H, s), 6.16 (1H, s) and 6.67, 7.42, 7.46 and 7.68 (each 1H, m) ppm.

EXAMPLE 46

1-(4-Methyl-2-oxazolyl)-1-(3-thienyl)ethanol

Following the general method of Example 2 and using 2-acetyl-4-methyloxazole, the title compound was obtained.

$^{13}$C Nmr (CDCl$_3$) 11.4, 28.5, 71.7, 120.8, 125.7, 126.1, 134.8, 136.3, 146.1 and 166.8 ppm.

EXAMPLE 47

1-(2-Benzofuranyl)-1-(4-methyl-5-thiazolyl)ethanol n-Butyllithium (2.5M solution in hexane, 1 equivalent) was added dropwise to a solution of 4-methyl-2-trimethylsilylthiazole (1 equivalent) in dry diethyl ether at −70° C. under an atmosphere of dry nitrogen. After 30 minutes, 2-acetylbenzofuran (1 equivalent) in diethyl ether was added. After 1 hour the mixture was allowed to warm to room temperature and was then quenched by the addition of saturated aqueous sodium hydrogen carbonate. Work up in the normal fashion and column chromatography on silica gel then afforded the title compound.

M.p. 139°–140° C.

Found: C, 64.65; H, 5.0; N, 5.3. C$_{14}$H$_{13}$NO$_2$S requires C, 64.85; H, 5.1; N, 5.4%

Following the general method of Example 47 and using the appropriate ketone, the compounds of Examples 48 to 50 were prepared.

EXAMPLE 48

1-(5-Methyl-2-furyl)-1-(4-methyl-5-thiazolyl)ethanol

M.p. 120°–123° C.

$^{13}$C Nmr (CDCl$_3$) 13.4, 15.8, 28.5, 70.3, 106.2, 107.5 138.3, 147.9, 149.3, 152.3 and 155.0 ppm.

EXAMPLE 49

1-(1-Methyl-3-pyrrolyl)-1-(4-methyl-5-thiazolyl)ethanol

M.p. 116°–117° C.

$^{13}$C Nmr (CDCl$_3$) 16.2, 30.2, 36.4, 70.9, 106.5, 119.2, 122.2, 130.4, 141.4, 147.0 and 148.5 ppm.

EXAMPLE 50

2-(4-Methyl-5-thiazolyl)-2-(2-thienyl)tetrahydrofuran

Using 4-chloro-1-(2-thienyl)-1-butanone.

$^1$H Nmr (CDCl$_3$) 2.0–2.16 (2H, m), 2.33 (3H, s), 2.5–2.62 and 2.68–2.8 (each 1H, m), 4.06 (2H, m), 6.9 (2H, m), 7.24 (1H, m) and 8.57 (1H, s) ppm.

Following the general method of Example 27 and using the appropriate alcohol, the compounds of Examples 51 to 53 were prepared.

EXAMPLE 51

1-(2,4-Dimethyl-5-oxazolyl)-1-(3-furyl)ethyl Ethyl Ether $^{13}$C Nmr (CDCl$_3$) 12.4, 13.8, 15.5, 25.4, 58.6, 72.9, 109.3, 129.5, 132.4, 139.5, 143.0, 146.9 and 158.9 ppm.

EXAMPLE 52

1-(2-Thiazolyl)-1-(2-thienyl)ethyl Methyl Ether $^{13}$C Nmr (CDCl$_3$) 25.3, 51.3, 79.8, 119.5, 125.5, 125.7, 126.5, 142.3, 147.8 and 176.2 ppm.

EXAMPLE 53

1-(4-Methyl-5-thiazolyl)-1-(2-thienyl)ethyl Methyl Ether

M.p. 49°–50° C.

Found: C, 55.1; H, 5.2; N, 5.8. $C_{11}H_{13}NOS_2$ requires C, 55.2; H, 5.5; N, 5.85%

The compounds of Example 54 to 57 were prepared by acid-catalyzed dehydration of the corresponding tertiary alcohols using methodology analogous to that employed in Examples 19 to 21.

EXAMPLE 54

1-(3,5-Dimethyl-4-isoxazolyl)-1-(3-thienyl)ethene

M.p. 35°–36° C.

Found: C, 64.5; H, 5.4; N, 6.7. $C_{11}H_{11}NOS$ requires C, 64.4; H, 5.4; N, 6.8%

EXAMPLE 55

1-(2,4-Dimethyl-5-thiazolyl)-1-(1-methyl-2-pyrrolyl)ethene $^{13}C$ Nmr (CDCl$_3$) 15.5, 19.0, 34.7, 107.5, 110.2, 117.5, 123.9, 131.7, 132.0, 133.4, 148.8 and 163.3 ppm.

EXAMPLE 56

1-(1-Methyl-3-pyrrolyl)-1-(4-methyl-5-thiazolyl)ethene $^{13}C$ Nmr (CDCl$_3$) 16.1, 36.2, 106.6, 112.7, 121.2, 122.7, 125.1, 131.9, 133.6, 149.8 and 149.9 ppm.

EXAMPLE 57

1-(2,4-Dimethyl-5-oxazolyl)-1-(3-furyl)-2-methyl-1-propene Hydrochloride

M.p. 125°–126° C.

$^{13}C$ Nmr (CDCl$_3$) 9.2, 13.4, 22.6, 23.1, 111.0, 112.1, 122.0, 125.4, 141.3, 143.4, 145.0, 149.4 and 162.4 ppm.

EXAMPLE 58

1-(2-Furyl)-1-(1,3,5-trimethyl-4-pyrazolyl)ethanol

4-Bromo-1,3,5-trimethylpyrazole was converted into the corresponding 4-lithio compound which was then reacted in situ with 2-acetylfuran.

M.p. 102°–105° C.

Found: C, 65.1; H, 7.4; N, 12.5. $C_{12}H_{16}N_2O_2$ requires C, 65.4; H, 7.3; N, 12.7%

EXAMPLE 59

1-(2,4-Dimethyl-5-oxazolyl)-1-(3-furyl)-2,2,2-trifluoroethanol

Tetrabutylammonium fluoride (250 mg) was added to a stirred solution of 2,4-dimethyl-5-oxazolyl 3-furyl ketone (1.7 g) and (trifluoromethyl)trimethylsilane (1.9 g) in dry tetrahydrofuran (30 ml) at –10° C. The mixture was allowed to warm to room temperature. After 45 minutes 6M hydrochloric acid (30 ml) was added. After 1 hour the mixture was basified by the addition of saturated aqueous sodium hydrogen carbonate and then extracted with dichloromethane. The material thus obtained was purified by flash chromatography and recrystallisation from diethyl ether.

M.p. 129°–130.5° C.

Found: C, 50.45; H, 3.7; N, 5.3. $C_{11}H_{10}F_3NO_3$ requires C, 50.6; H, 3.9; N, 5.4%

EXAMPLE 60

1-(2,4-Dimethyl-5-thiazolyl)-1-(1-methyl-2-pyrrolyl)ethanol n-Butyllithium (2.5M solution in hexanes, 20 ml) in dry diethyl ether was cooled to –70° C. under dry nitrogen and TMEDA (5.8 g) was added. After 5 minutes, 1-methylpyrrole (5.4 g) in diethyl ether was added dropwise. After a further 15 minutes, 5-acetyl-2,4-dimethylthiazole (4.5 ml) was added dropwise. After 30 minutes the mixture was allowed to warm to room temperature and was then worked up in the usual fashion.

M.p. 194°–197° C. (dec.).

$^{13}C$ Nmr (CDCl$_3$) 14.4, 18.8, 31.6, 35.5, 70.7, 106.1, 108.0, 124.7, 135.0, 137.5, 145.7 and 162.5 ppm.

EXAMPLE 61

1-(5-(2-Hydroxethyl)-4-methyl-2-thiazolyl)-1-(3-thienyl)ethanol n-Butyllithium (2.5M solution in hexanes, 75 mmoles) was added to a stirred solution of 5-(2-hydroxyethyl)-4-methylthiazole (35 mmoles) in dry tetrahydrofuran (80 ml) at –70° C. under an atmosphere of dry nitrogen. After 30 minutes, 3-acetylthiophene (38 mmoles) in dry tetrahydrofuran (10 ml) was added dropwise. After 1 hour the mixture was allowed to warm to room temperature and was then stirred overnight. The normal work-up followed by column chromatography then gave the title compound.

M.p. 127°–129° C.

$^{13}C$ Nmr (d$_6$-DMDO) 15.7, 30.3, 30.8, 62.1, 74.5, 120.9, 126.4, 127.4, 129.0, 148.0, 149.6 and 175.4 ppm.

EXAMPLE 62

1-(5-(2-Acetoxyethyl)-4-methyl-2-thiazolyl)-1-(3-thienyl)ethanol

The product from Example 61 was treated at room temperature with acetyl chloride in dichloromethane in the presence of triethylamine.

$^{13}C$ Nmr (CDCl$_3$) 14.9, 20.9, 26.0, 30.7, 64.0, 74.4, 121.1, 126.0, 126.1, 127.5, 147.5, 148.6, 170.7 and 173.7 ppm.

Found: C, 54.1; H, 5.6; N, 4.45. $C_{14}H_{17}NO_3S_2$ requires C, 54.0; H, 5.5; N, 4.5%

EXAMPLE 63

1-(4-Bromo-3-furyl)-1-(2,4-dimethyl-5-oxazolyl)ethanol

Following the general method of Example 1a but using 5-acetyl-2,4-dimethyloxazole and 4-bromo-3-lithiofuran (Liebigs Ann. Chem., 1986, 625–637), the title compound was prepared.

M.p. 124°–125° C.

$^{13}C$ Nmr (CDCl$_3$) 12.3, 13.7, 27.6, 68.5, 99.0, 129.9, 132.0, 140.4, 142.7, 146.9 and 159.0 ppm.

EXAMPLE 64

1-(5-Methoxymethyl-4-methyl-2-thiazolyl)-1-(3-thienyl)ethanol

The title compound was prepared by following the general method of Example 36 but using 3-acetylthiophene and 5-methoxymethyl-4-methylthiazole.

M.p. 71°–73° C.

$^{13}$C Nmr (CDCl$_3$) 15.1, 30.7, 57.9, 65.9, 74.4, 121.1, 125.9, 126.0, 128.5, 147.3, 149.5 and 175.4 ppm.

EXAMPLE 65

1-Azido-1-(3-furyl)-1-(4-methyl-5-oxazolyl)ethane 1-(3-Furyl)-1-(4-methyl-5-oxazolyl)ethanol (1 g) was suspended in benzene (4 ml). Trimethylsilylazide (822 µl) was added followed by borontrifluoride diethyletherate (770 µl). The mixture was stirred overnight at room temperature, then poured into water and extracted to give the title compound.

$^{13}$C Nmr (CDCl$_3$) 12.4, 25.9, 59.9, 108.8, 127.4, 132.5, 139.6, 143.9, 146.1 and 149.0 ppm.

EXAMPLE 66

1-(3-Furyl)-1-(4-methyl-5-oxazolyl)ethylamine

The product from Example 65 in ethanol was hydrogenated in the presence of 10% palladium-on-charcoal to give the title compound.

M.p. 82.5°–83.5° C.

$^{13}$C Nmr (CDCl$_3$) 12.7, 29.9, 50.5, 109.0, 129.5, 132.4, 138.4, 143.3, 148.0 and 150.6 ppm.

EXAMPLE 67

1-Azido-1-(2-thiazolyl)-1-(3-thienyl)ethane

The title compound was obtained starting from 1-(2-thiazolyl)-1-(3-thienyl)ethanol and following the general method of Example 65.

$^{13}$C Nmr (CDCl$_3$) 26.8, 66.2, 119.8, 122.4, 126.0, 126.6, 143.0, 143.2 and 173.4 ppm.

EXAMPLE 68

1-(2-Thiazolyl)-1-(3-thienyl)ethylamine

Reduction of the product from Example 67 as in Example 66 gave the title compound.

$^{13}$C Nmr (CDCl$_3$) 31.6, 57.4, 118.8, 120.3, 125.8, 126.0, 142.4, 148.4 and 179.7 ppm.

EXAMPLE 69

1-(2,4-Dimethyl-5-oxazolyl)-1-(3-furyl)-
2,2,2-trifluoroethylamine 1-(2,4-Dimethyl-5-oxazolyl)-1-(3-furyl)-2,2,2-trifluoroethanol (160 mg) was suspended in benzene (2 ml) at room temperature. Diphenylphosphoryl azide (156 µl) was added, followed by 1,8-diazabicyclo [5.4.0] undec-7-ene (112µl). The mixture was stirred for 20 hours and was then diluted with ethyl acetate and water. Work-up in the usual fashion then gave 1-azido-1-(2,4-dimethyl-5-oxazolyl-1-(3-furyl)-2, 2,2-trifluoroethane. Reduction of this azide using the method of Example 66 then gave the title compound.

$^{13}$C Nmr (CDCl$_3$) 12.4, 13.8, 58.0, (q, J 30 Hz), 109.9, 122.8, 125.7, (q, J 286 Hz), 135.0, 141.0, 141.3, 143.4 and 159.8 ppm.

EXAMPLE 70

N-[1-(1-(3-Furyl)-1-(4-methyl-5-oxazolyl)-
ethyl)]acetamide

The product from Example 66 was treated with acetyl chloride in the presence of triethylamine to give the title compound.

$^{13}$C Nmr (CDCl$_3$) 12.6, 23.8, 25.6, 52.5, 108.9, 129.4, 130.8, 139.5, 143.6, 147.1 148.0 and 168.9 ppm.

PHARMACY EXAMPLES

The following examples illustrate suitable pharmaceutical compositions to be used in the method of the invention.

| Composition 1 - Tablets | |
|---|---|
| Compound of Example 5 | 10 g |
| Lactose | 94 g |
| Microcrystalline cellulose | 86 g |
| Polyvinylpyrrolidone | 8 g |
| Magnesium stearate | 2 g |

The compound of Example 5, lactose, cellulose and polyvinylpyrrolidone are sieved and blended. The magnesium stearate is sieved and then blended into the above mixture. Compression using suitable punches then yields 1000 tablets each containing 10 mg of the active ingredient. If desired, the obtained tablets can then be film coated.

| Composition 2 - Tablets | |
|---|---|
| Compound of Example 46 | 50 g |
| Lactose | 80 g |
| Microcrystalline cellulose | 20 g |
| Potato starch | 40 g |
| Polyvinylpyrrolidone | 8 g |
| Magnesium stearate | 2 g |

The compound of Example 46, lactose, cellulose and part of the starch are mixed and granulated with 10% starch paste. The resulting mixture is dried and blended with the remaining starch, the polyvinylpyrrolidone and the sieved magnesium stearate. The resulting blend is then compressed to give 1000 tablets each containing 50 mg of the active ingredient.

| Composition 3 - Capsules | |
|---|---|
| Compound of Example 31 | 100 g |
| Pregelatinised starch | 98 g |
| Magnesium stearate | 2 g |

The compound of Example 31 and the starch are sieved, blended together and then lubricated with the sieved magnesium stearate. The blend is used to fill 1000 hard gelatine capsules of a suitable size. Each capsule contains 100 mg of the active ingredient.

| Composition 4 - Injection Formulation | |
|---|---|
| Compound of Example 66 | 0.5 to 10 g |
| Polyethoxylated castor oil | 15 g |
| Water for injection   ad | 100 g |

Sodium chloride may be added to adjust the tonicity of the solution and the pH may be adjusted to that of maximum stability and/or facilitate solution of the compound of the invention using dilute acid or alkali or by the addition of suitable buffer salts. Antioxidants and metal chelating salts may also be included.

The solution is prepared, clarified and filled into appropriate size bottles and sealed. The formulation is sterilised by heating in an autoclave. Alternatively, the solution may be sterilised by filtration and filled into sterile bottles under aseptic conditions. The solution may be packed under a nitrogen blanket.

| Composition 5 - Injection Formulation | |
|---|---|
| Compound of Example 5 | 0.5 to 10 g |
| Polyethoxylated castor oil | 15 g |
| Propylene glycol | 20 g |
| Polyoxyethylene-polyoxypropylene block copolymer (Pluronic F68) | 10 g |
| Water for injection    ad | 100 g |

The compound of the invention is added to a mixture of polyethoxylated castor oil, propylene glycol and Pluronic F68. The mixture is gently heated until a clear solution is obtained. This solution is sterilised by heating in an autoclave or alternatively, by the process of filtration. A concentrated sterile solution is thus obtained, which is suitable for dilution with sterile water in order to form a composition suitable for parenteral administration.

| Composition 6 - Injection Formulation | |
|---|---|
| Compound of Example 59 | 0.5 to 10 g |
| Hydroxypropyl-β-cyclodextrin | 10 g |
| Water for injection    ad | 100 g |

Water for injection is added to a mixture of the compound of the invention and hydroxypropyl-β-cyclodextrin. The mixture is gently stirred until a clear solution is obtained. The solution is filled into bottles which are then sealed and sterilised by heating in an autoclave or alternatively, by the process of filtration.

We claim:

1. A method for the treatment of acute and chronic neuropsychiatric disorders characterised by progressive processes that lead to neuronal cell death and dysfunction by administering to a host in need of such treatment a sufficient amount of a compound having the general formula (1)

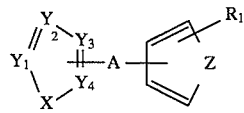         (1)

wherein:

X is O, S, Se, or $NR_2$;

$Y_1, Y_2, Y_3, Y_4$ independently are N or $CR_2$;

Z is O, S, Se, $NR_2$ or C=N;

$R_1$ is at least one group selected from the group consisting of H, lower alkyl, lower acyl, halogen, lower alkoxy and $CF_3$, or $R_1$ and the ring

together represent a fused benzo ring unsubtituted or further substituted;

$R_2$ is H, lower alkyl, lower alkoxy-lower alkyl, hydroxy-lower alkyl, lower acyloxy-lower alkyl, aryl-lower alkyl or $CF_3$ and when more than one $R_2$ groups are present these may be selected independently; and A is

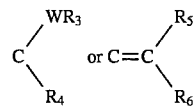

wherein

W is O, S, NH or N-lower alkyl, $R_3$ is H, lower alkyl or lower acyl, $R_4$ is lower alkyl, aryl-lower alkyl, cyclopropyl or lower perfluoroalkyl, or $R_3$ and $R_4$ together form a ring

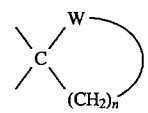

wherein n is 2, 3 or 4, $R_5$ and $R_6$ independently are H, lower alkyl, or aryl-lower alkyl;

with the proviso that at least one of X, $Y_1$, $Y_2$, $Y_3$ or $Y_4$ is nitrogen and that the ring

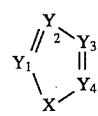

is not 1-methyl-2-imidazolyl;

geometric and optical isomers and racemates thereof where such isomers exist, as well as pharmaceutically acceptable acid addition salts thereof and solvates thereof.

* * * * *